US009411244B2

(12) United States Patent
Ryzhikov et al.

(10) Patent No.: US 9,411,244 B2
(45) Date of Patent: Aug. 9, 2016

(54) OPTICAL SYSTEM, INSPECTION SYSTEM AND MANUFACTURING METHOD

(71) Applicant: ASML HOLDING N.V., Veldhoven (NL)

(72) Inventors: Lev Ryzhikov, Norwalk, CT (US); Yuli Vladimirsky, Weston, CT (US); James H. Walsh, Newtown, CT (US)

(73) Assignee: ASML HOLDING N.V., Veldhoven (NL)

( * ) Notice: Subject to any disclaimer, the term of this patent is extended or adjusted under 35 U.S.C. 154(b) by 157 days.

(21) Appl. No.: 14/107,819

(22) Filed: Dec. 16, 2013

(65) Prior Publication Data

US 2014/0098356 A1     Apr. 10, 2014

Related U.S. Application Data

(63) Continuation of application No. 13/105,364, filed on May 11, 2011, now Pat. No. 8,692,977.

(60) Provisional application No. 61/334,286, filed on May 13, 2010.

(51) Int. Cl.
*G03B 27/54* (2006.01)
*G03B 27/42* (2006.01)
(Continued)

(52) U.S. Cl.
CPC .............. *G03F 7/7015* (2013.01); *G01N 21/94* (2013.01); *G02B 13/04* (2013.01); *G02B 13/18* (2013.01); *G03F 1/84* (2013.01); *G03F 7/7085* (2013.01); *G03F 7/70908* (2013.01)

(58) Field of Classification Search
CPC .... G03F 7/70908; G03F 7/7085; G03F 7/015
USPC ............... 355/30, 52, 53, 55, 67; 356/302; 359/365, 684, 717
See application file for complete search history.

(56) References Cited

U.S. PATENT DOCUMENTS 4,214,815 A     7/1980   Shimokura
5,668,669 A *   9/1997   Ohtake et al. ................ 359/684
(Continued)

FOREIGN PATENT DOCUMENTS

CN          1585907        2/2005
CN        101034199        9/2007
(Continued)

OTHER PUBLICATIONS

Japanese Office Action dated Oct. 15, 2014 in corresponding Japanese Patent Application No. 2011-103542.
(Continued)

*Primary Examiner* — Hung Henry Nguyen
(74) *Attorney, Agent, or Firm* — Pillsbury Winthrop Shaw Pittman LLP

(57) ABSTRACT

Systems and methods for inspection are provided utilizing a wide angle optical system. The optical system includes a wide angle input lens group and an output lens group. The wide angle input lens group is configured to receive wide-angle radiation, e.g., having an angular spread of 60 degrees or more, from an object surface, and produce imageable radiation. The wide angle input lens group is arranged such that no intermediate focused image is formed within or after the wide angle input lens group. The output lens group is configured to receive the imageable radiation from the wide angle input lens group and focus the imageable radiation onto an image plane to image at least part of the object surface. A detector receives the image of the at least part of the object surface and, based on the received image, detects, for example, contamination on the object surface.

20 Claims, 3 Drawing Sheets

(51) Int. Cl.
*G02B 15/14* (2006.01)
*G03F 7/20* (2006.01)
*G02B 13/04* (2006.01)
*G02B 13/18* (2006.01)
*G03F 1/84* (2012.01)
*G01N 21/94* (2006.01)

(56) References Cited

U.S. PATENT DOCUMENTS

| | | | |
|---|---|---|---|
| 6,774,944 B1 | 8/2004 | Fukuyama | |
| 7,177,012 B2 | 2/2007 | Bleeker et al. | |
| 7,177,020 B2 * | 2/2007 | Morioka et al. | 356/300 |
| 7,280,283 B1 | 10/2007 | Kasai | |
| 7,408,703 B2 * | 8/2008 | Matsuki et al. | 359/365 |
| 7,433,033 B2 | 10/2008 | Bleeker et al. | |
| 7,505,211 B2 | 3/2009 | Horneber | |
| 7,586,596 B2 | 9/2009 | Guetta et al. | |
| 7,912,658 B2 | 3/2011 | Biellak et al. | |
| 8,189,203 B2 | 5/2012 | Shmarev et al. | |
| 8,237,842 B2 * | 8/2012 | Wakamiya | 348/335 |
| 2006/0082752 A1 | 4/2006 | Bleeker et al. | |
| 2007/0258086 A1 | 11/2007 | Bleeker et al. | |
| 2008/0291531 A1 * | 11/2008 | Heimer | 359/351 |
| 2009/0244701 A1 | 10/2009 | Gohman | |
| 2009/0251786 A1 | 10/2009 | Ryzhikov et al. | |
| 2010/0045955 A1 | 2/2010 | Vladimirsky et al. | |
| 2011/0102913 A1 | 5/2011 | Neil | |

FOREIGN PATENT DOCUMENTS

| | | |
|---|---|---|
| CN | 101403820 | 4/2009 |
| CN | 101408664 | 4/2009 |
| JP | H08-313803 | 11/1996 |
| JP | H10-010427 | 1/1998 |
| JP | 2000-235145 | 8/2000 |
| JP | 2005-134158 | 5/2005 |
| JP | 2005-268823 | 9/2005 |
| JP | 2007-333729 | 12/2007 |
| TW | 200921083 | 5/2009 |
| WO | 2006-064428 | 6/2006 |

OTHER PUBLICATIONS

Chinese Office Action dated Jun. 4, 2014 in corresponding Chinese Patent Application No. 201110112084.4.
Taiwan Office Action dated Nov. 11, 2015 in corresponding Taiwan Patent Application No. 100114132.

* cited by examiner

OPTICAL SYSTEM, INSPECTION SYSTEM AND MANUFACTURING METHOD

This application is a continuation of U.S. patent application Ser. No. 13/105,364, filed on May 11, 2011, now U.S. Pat. No. 8,692,977, which claims priority and benefit under 35 U.S.C. §119(e) to U.S. Provisional Patent Application No. 61/334,286, filed on May 13, 2010. The content of each of the foregoing applications is incorporated herein in its entirety by reference.

FIELD

The present invention relates to an optical system, an inspection system having the optical system, a lithographic apparatus having such an inspection system, and a manufacturing method.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

The imaging of the pattern (which typically includes micron or nanometer sized structures) can be very sensitive to dust or other contamination of the patterning device and/or the substrate. Therefore, before imaging, the patterning device (and/or a pellicle protecting the small structures thereof) and/or substrate may be tested for contamination, in particular for particles, using a contamination inspection system. If a particle is detected on the patterning device or on the substrate, the particle may be accepted (thereby accepting a possible fault area on the substrate), or it may be removed, or the patterning device or substrate may be rejected.

SUMMARY

Current contamination inspection systems for inspecting a surface of an object, e.g., a reticle, a pellicle associated with a reticle and/or a substrate, use scattered radiation techniques. In this technique, a laser beam is focused on the object and radiation that is scattered from the object and received by an optical system for further projection onto an image plane.

In order to image, for example, a full surface of an object in a single shot, the inspection system may have an optical system provided with a wide angle lens having, e.g., an angle-of-view at least equal to 60 degrees. Typically, such a wide angle lens works best when the object is positioned at infinity.

When such a wide angle lens is used for close-up and short finite working distances, e.g., in particle inspection systems, the wide angle lens forms an image of insufficient quality suffering from relatively high aberrations. To improve the image quality, an optical relay lens group including an input condenser and an output condenser may be used in series with the wide angle lens. In this arrangement, radiation from the wide angle lens (forming an intermediate low-quality image) is received by the input condenser and passed onto the output condenser to form a relatively better quality image of the object. However, this combination of wide angle lens and optical relay lens group may be bulky and may suffer from low modulation transfer function (MTF) contrast and vignetting, particularly at field edges for high resolution imaging settings. Also, such a combination may not support optical reversibility such that the magnification of the optical system can be reversed by changing the arrangement of the elements within, e.g., the optical relay lens group.

Accordingly, it would be advantageous, for example, to provide a wide angle optical system, e.g., in a particle inspection system, that can support full field or full surface imaging for finite short working distances, and provide an image of an object surface with high MTF contrast and high resolution.

According to an aspect, there is provided an optical system including a wide angle input lens group and an output lens group. The wide angle input lens group is configured to receive radiation, e.g., having an angular spread of 60 degrees or more from an object surface, and produce imageable radiation. In an embodiment, the wide angle input lens group is arranged such that no intermediate focused image is formed within or after the wide angle input lens group. The output lens group is configured to receive the imageable radiation from the wide angle input lens group and focus this radiation onto an image plane to image at least part of the object surface. The image plane may be coplanar with a detector which is configured to receive the image of the at least part of the object surface, and based on the received image, to detect contamination or other abnormality on the object surface. The object may be, for example, a reticle, a pellicle associated with a reticle, a substrate, reticle holder, or a table in a lithography system.

In an embodiment, the wide angle input lens group includes a front optical element and a doublet having an aspheric surface. In an embodiment, the output lens group includes a doublet and a last lens element having an aspheric surface. The wide angle input lens group and output lens group may be configured to be interchangeably arranged in the optical system to change the magnification of the optical system. The optical system may be arranged such that the optical system is not telecentric.

According to an aspect, there is provided an inspection system to inspect a surface of an object, the inspection system including an optical system and a detector. The optical system includes a wide angle input lens group which is configured to receive radiation, e.g., having an angular spread of 60 degrees or more, from the object surface, and produce imageable radiation therefrom. In an embodiment, the wide angle input lens group is arranged such that no intermediate focused image is formed within or after the wide angle input lens group. The optical system further includes an output lens group which is configured to receive the imageable radiation from the wide angle input lens group and focus the imageable radiation onto an image plane to image at least part of the object surface. The detector of the inspection system is configured to receive the image of the at least part of the object surface, and based on the received image, detect contamination, an abnormality of the object surface, and/or a pattern (e.g., a bar code) on the object surface. The inspection system may further include an illumination source which provides an illumination beam to illuminate the surface of the object. The object may be a reticle, a pellicle associated with a reticle, a substrate, or a table in a lithography system.

According to an aspect, there is provided a lithographic apparatus including a support structure configured to hold a patterning device. The patterning device is configured to spatially modulate the beam with a pattern. The lithographic apparatus further includes a substrate table configured to hold a substrate, a projection system to project the patterned beam onto a target portion of the substrate, and an inspection system to inspect an object surface. The inspection system includes an optical system and a detector. The optical system includes a wide angle input lens group which is configured to receive radiation, e.g., having an angular spread of 60 degrees or more, from the object surface, and produce imageable radiation therefrom. In an embodiment, the wide angle input lens group is arranged such that no intermediate focused image is formed within or after the wide angle input lens group. The optical system further includes an output lens group which is configured to receive the imageable radiation from the wide angle input lens group and focus the imageable radiation onto an image plane to image at least part of the object surface. The detector of the inspection system is configured to receive the image of the at least part of the object surface and, based on the received image, detect contamination, an abnormality of the object surface, and/or a pattern on the object surface. The inspection system may further include an illumination source which provides an illumination beam to illuminate the surface of the object. The inspected object may be a patterning device, a pellicle associated with a patterning device, a substrate, or a table in the lithographic apparatus, According to an aspect, there is provided a manufacturing method including projecting a patterned beam of radiation onto a target portion of a substrate, and inspecting an object surface (e.g., a reticle, a pellicle associated with a reticle, or a substrate). The inspecting includes receiving radiation from the object surface at a wide angle input lens group to produce imageable radiation therefrom, such that there is no intermediate focused image formed within or after the wide angle input lens group. The inspecting further includes focusing the imageable radiation onto an image plane to image at least part of the object surface, and detecting contamination, an abnormality of the object surface, and/or a pattern on the object surface based on the image of the at least part of the object surface. In an embodiment, the inspecting further includes illuminating the surface of the object with an illumination beam.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
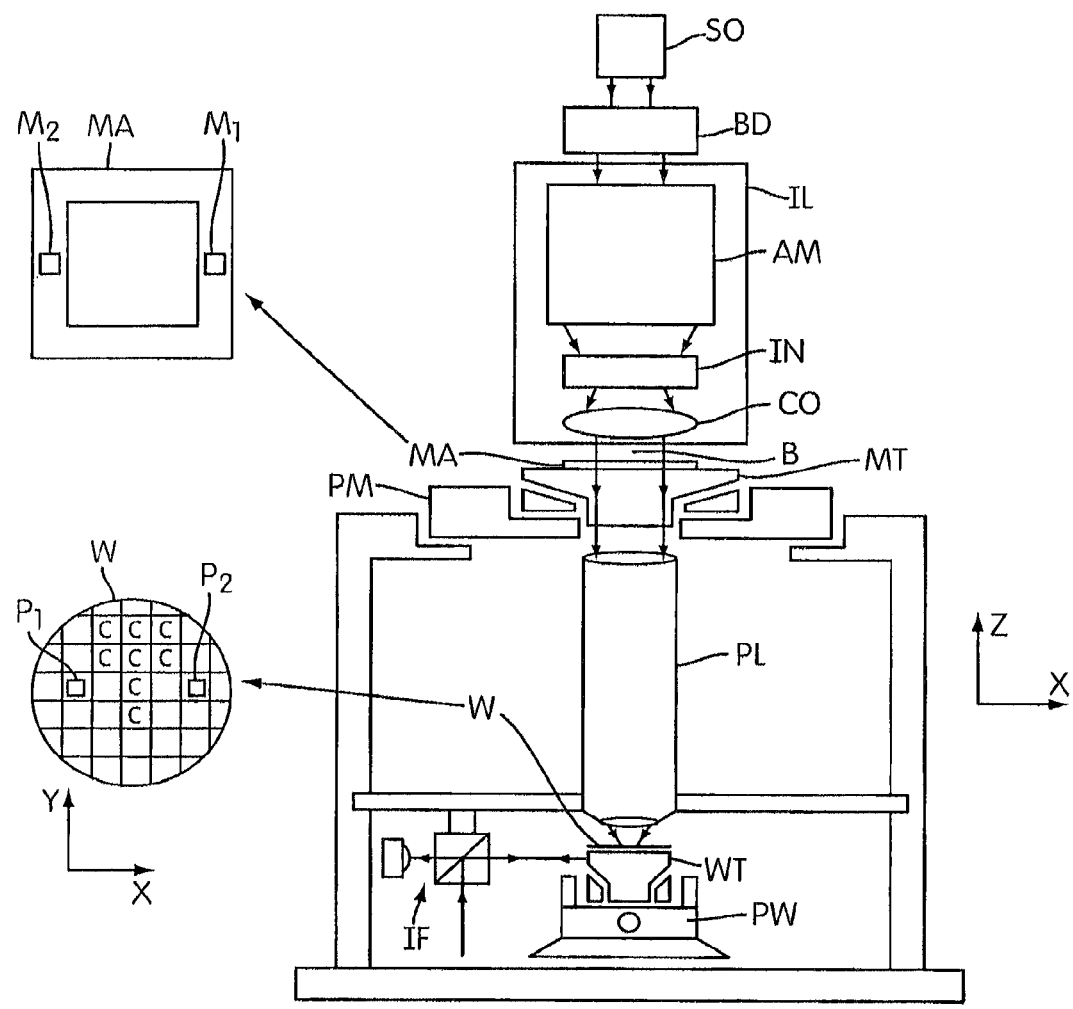
FIG. 1 schematically depicts a lithographic apparatus according to an embodiment of the invention.

FIG. 1 schematically depicts a lithographic apparatus according to an embodiment of the invention. The apparatus comprises an illumination system (illuminator) IL configured to condition a radiation beam B (e.g. UV radiation or DUV radiation); a support structure (e.g. a mask table) MT constructed to hold a patterning device (e.g. a mask) MA and connected to a first positioner PM configured to accurately position the patterning device in accordance with certain parameters; a substrate table (e.g. a wafer table) WT constructed to hold a substrate (e.g. a resist-coated wafer) W and connected to a second positioner PW configured to accurately position the substrate in accordance with certain parameters; and a projection system (e.g. a refractive projection lens system) PS configured to project a pattern imparted to the radiation beam B by patterning device MA onto a target portion C (e.g. comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables (and/or two or more support structures). In such "multiple stage" machines the additional tables/support structure may be used in parallel, or preparatory steps may be carried out on one or more tables/support structure while one or more other tables/support structures are being used for exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD configured to adjust the angular intensity distribution of the radiation beam. Generally, at least the outer and/or inner radial extent (commonly referred to as a-outer and o-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross-section.

The radiation beam B is incident on the patterning device (e.g., mask) MA, which is held on the support structure (e.g., mask table) MT, and is patterned by the patterning device. Having traversed the patterning device MA, the radiation beam B passes through the projection system PS, which focuses the beam onto a target portion C of the substrate W. With the aid of the second positioner PW and position sensor IF (e.g. an interferometric device, linear encoder or capacitive sensor), the substrate table WT can be moved accurately, e.g. so as to position different target portions C in the path of the radiation beam B. Similarly, the first positioner PM and another position sensor (which is not explicitly depicted in FIG. 1) can be used to accurately position the patterning device MA with respect to the path of the radiation beam B, e.g. after mechanical retrieval from a mask library, or during a scan. In general, movement of the support structure MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the support structure MT may be connected to a short-stroke actuator only, or may be fixed. Patterning device MA and substrate W may be aligned using patterning device alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device MA, the patterning device alignment marks may be located between the dies.

The depicted apparatus could be used in at least one of the following modes:

1. In step mode, the support structure MT and the substrate table WT are kept essentially stationary, while an entire pattern imparted to the radiation beam is projected onto a target portion C at one time (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the radiation beam is projected onto a target portion C (i.e. a single dynamic exposure). The velocity and direction of the substrate table WT relative to the support structure MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
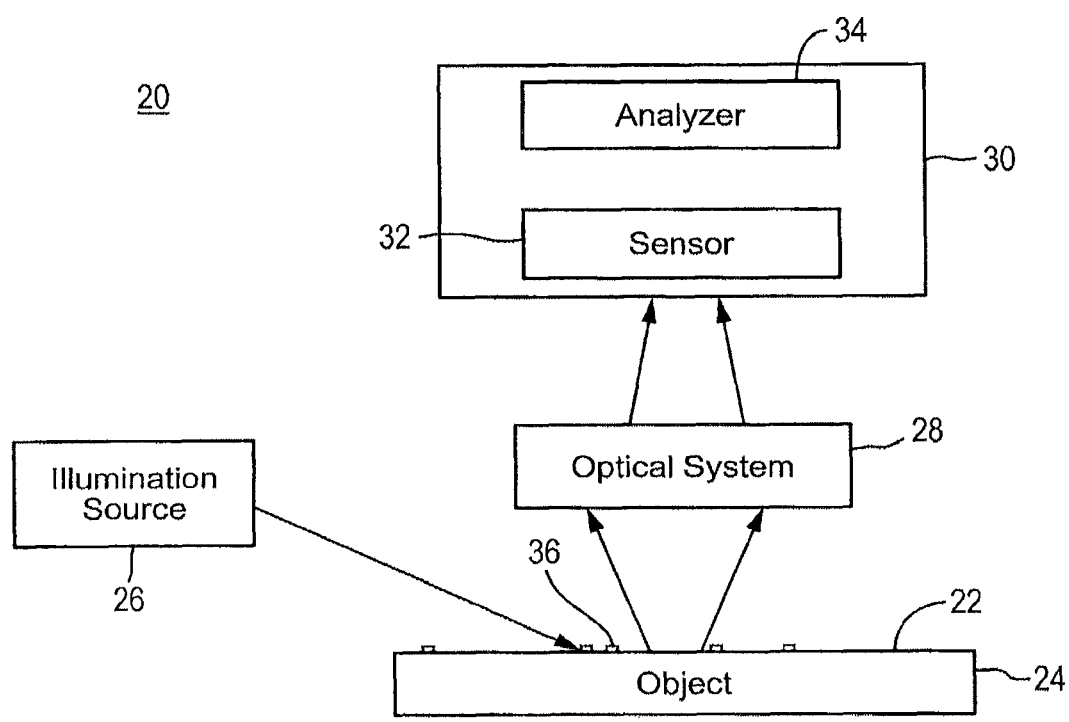
FIG. 2 schematically depicts an inspection system according to an embodiment of the invention.

FIG. 2 illustrates a system for inspection of a surface of an object, according to an embodiment of the present invention. In an embodiment, the inspection system is used to detect contamination, an abnormality of the object surface, and/or a pattern on the object surface. In an embodiment, contamination may include, for example, particles. In an embodiment, an abnormality of the object surface may include, for example, a defect of a feature of a reticle pattern. In an embodiment, a pattern on the object surface may include, for example, a bar code, a reticle pattern, or alignment mark.

The inspection system 20 may be used for inspection purposes of a surface 22 of object 24, which may be, for example, a reticle, a pellicle protecting a patterned or unpatterned side of a reticle, a substrate, or a holder, chuck or table (e.g., any part of a substrate table, measurement sensor table, or patterning device table). The inspection system is shown as a separate system 20 but it may be provided as an in-tool system and integrated with the lithographic apparatus, e.g., as described with reference to FIG. 1. As an in-tool system, it may perform an inspection of the surface 22 of object 24 prior to a lithographic process.

In an embodiment, the inspection system 20 includes an illumination source 26, an optical system 28, and a detector 30. Illumination source 26 provides an illumination beam to illuminate surface 22 of object 24. In FIG. 2, only one illumination source 26 is shown, but there may be more than one illumination sources. Alternatively, the inspection system 20 may not have a separate illumination source 26 and surface 22 may be irradiated by the ambient radiation or radiation provided by a source separate from the inspection system 20. Illumination source 26 can be, for example, a standard light emitting diode (LED), flash light emitting diode (flash LED), or laser diode, but is not to be limited to these as other types of illumination source may be used.

The optical system 28 may include, as will be described in detail later, an optic or optics such as one or more lens groups. The optical system 28 receives or intercepts radiation (e.g., scattered radiation) from the illuminated object surface 22, to project an image of the surface 22 of object 24 onto detector 30, and to magnify or de-magnify as necessary. The image is projected from optical system 28 onto a sensor 32 of detector 30 and subsequently, the image data recorded on the sensor 32 is analyzed by an analyzer 34 to detect contamination, an abnormality, a pattern, or any combination thereof, on the object surface 22. The image of the object surface 22 may be a full field image to capture the complete surface in one shot, thus providing expedient data collection and shortening object inspection time. For example, the inspection system may capture a 160 mm×160 mm reticle in one shot. Such a short single-frame acquisition time allows for multi-frame sequential imagery and image enhancement techniques such as sub-pixel resolution processing. Full field images obtained using such techniques are high resolution images that allow for accurate detection of, e.g., real particle shapes and sizes, as well as particle positioning.

If the surface 22 is too large or if sensor 32 does not have enough capacity for a single projection of a full field image, two or more partial images can be obtained for an effective full field image. Sensor 32 can be a linear or large area sensor, and can include, but is not to be limited to, a CMOS sensor array or a charge-coupled device (CCD). For example, sensor 32 can include a linear CCD or a large area CCD.

The full field image of object surface 22 can be analyzed by analyzer 34 for, for example, particles (e.g., particles 36 shown in FIG. 2), other contamination, an abnormality (e.g., a broken reticle pattern feature) or a pattern (e.g., a bar code). For example, analyzer 34 can be used to determine sizes and positions of detected particles and/or abnormalities. The determination of particle size and position can be used to reject object 24 (e.g., a reticle or a pellicle covering a reticle), e.g., if a determined size or position is outside of a certain range or other limit. In an embodiment, analyzer 34 is a typical computer system including analyzer software and a general purpose processor to execute the analyzer software. Alternatively, the computer system may include a special purpose processor configured to perform the image analysis as described above.

As discussed above, the inspection system 20 can be integrated with a lithographic apparatus to inspect, e.g., a reticle, a pellicle covering a reticle, or a substrate. In such lithographic apparatus, there may be separate inspection systems to simultaneously inspect those objects, resulting in higher throughput, or there may be a single inspection system to inspect the objects in a serial manner. When used in a lithography system, the inspection system 20 may be used for other functions, such as for metrology purposes. Reticle, and even substrate, pre-alignment can be accomplished by having system 20 detect appropriate alignment targets. Reticle (or substrate) identification can be accomplished by reading and interpreting one or more bar codes (e.g., one-dimensional bar codes, two-dimensional bar codes, etc.) located on a reticle (or substrate) surface.

Figure 3:
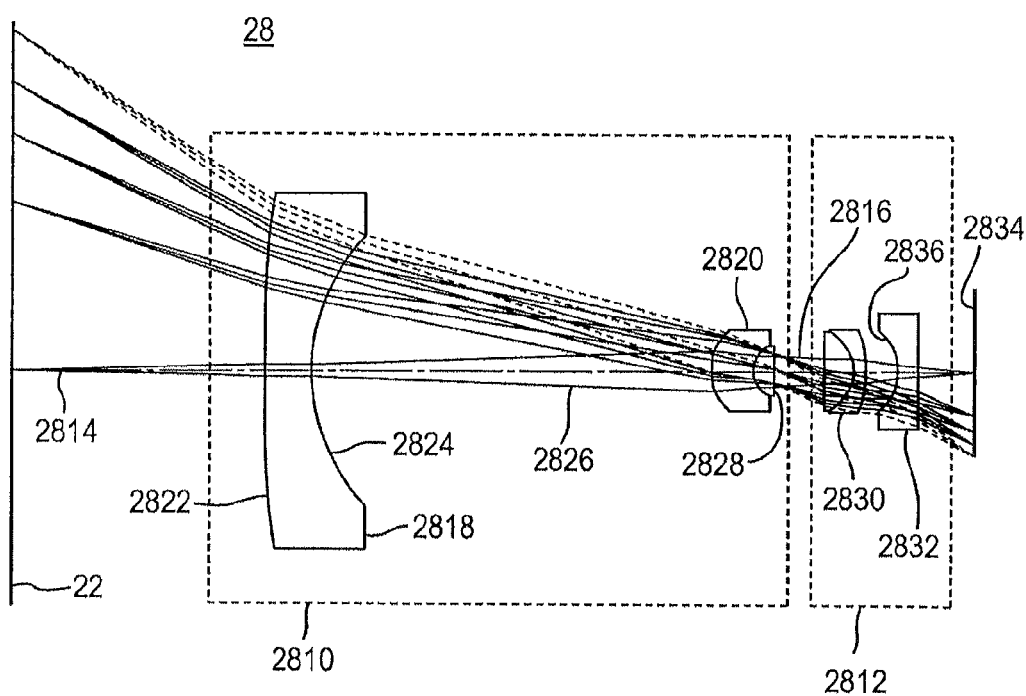
FIG. 3 schematically depicts an optical system according to an embodiment of the invention.

FIG. 3 illustrates optical system 28 in greater detail. In an embodiment, optical system 28 is a relay lens group including an input lens group (or input condenser) 2810 and an output lens group (or output condenser) 2812. In an embodiment, the input lens group 2810 and the output lens group 2812 are arranged such that the optical system 28 is not telecentric. In an embodiment, optical system 28 includes more than one input lens group 2810, more than one output lens group 2812, or both. Input lens group 2810 receives radiation 2814 from the illuminated surface 22 of object 24 and produces imageable radiation 2816 (e.g., a beam such as a collimated beam or a beam with a focus essentially at infinite) which is directed and incident on output lens group 2812. In an embodiment, input lens group 2810 includes a wide angle front lens element 2818 on the side of the input lens group 2810 receiving the radiation from surface 22, and a doublet 2820 on the other side of the input lens group 2810.

Wide angle front lens element 2818 may be arranged to have a convex surface 2822 on the side receiving the radiation 2814 and a concave surface 2824 on the other side, such that the front lens element 2818 has a wide angle-of-view of about 60 degrees or more, thereby facilitating imaging of the complete inspected surface 22 (or at least a significant portion of it) at a single time. Both surfaces 2822, 2824 may have an aspheric surface formed thereon for low spherical and chromatic aberrations. Wide angle front lens element 2818 may include multiple optical elements. One or more of the multiple optical elements may have one or more aspheric surfaces. Functionally, wide angle front lens element 2818 receives radiation from surface 22 and diverges the received radiation (to form diverged radiation 2826) for projection onto doublet 2820 such that no intermediate focused image of the object surface 22 is formed within input lens group 2810 including between front lens element 2818 and doublet 2820, or formed after the input lens group 2810.

Radiation 2826 after passing through doublet 2820 is converted into imageable radiation 2816 (e.g., a beam such as a collimated beam or a beam focused essentially at infinity). An aspheric surface may be formed on a concave surface 2828 of doublet 2820 facing the output lens group 2812, which facilitates pupil aberration correction and improves modulation transfer function (MTF) of the optical system 28. The radiation receiving side of the doublet 2820 may have a convex surface. Instead of or in addition to doublet 2820 and front lens element 2818, one or more multi-element optics with one or more aspheric surfaces may be used in the input lens group 2810 to perform the optical functions described above. An aperture stop may be located between the input lens group 2810 and the output lens group 2812 at the Fourier or field plane of the input lens group 2810.

In an embodiment, output lens group 2812 includes a doublet 2830 and last lens element 2832. Output lens group 2812 receives and converges the radiation 2816 to focus it onto an image plane 2834 to form an image of the object surface 22. An aspheric surface may be formed on the concave surface 2836 of the last lens element 2832 facing doublet 2830 which allows for generating a low-distortion high-resolution image of surface 22 formed on the image plane 2834. The image plane 2834 may be the surface of the sensor 32. Output lens group 2812 may be arranged such that output lens group 2812 is quasi-symmetric with the input lens group 2810, i.e., the input lens group 2810 and output lens group 2812 are configured such that they can be interchangeably arranged in the optical system 28 to adjust, e.g. reverse, the magnification of the optical system 28. Instead of or in addition to doublet 2830 and last lens element 2832, one or more multi-element optics may be used in the output lens group 2812 to perform the optical functions described above. One or more of the multi-element optics may an aspheric surface.

Unlike a conventional wide angle optical system utilizing a wide angle lens forming a poor quality image which is improved by a relay lens group, the above described optical system including a wide angle input lens group and an output lens group has a simpler construction and eliminates the need for a separate wide angle lens group by integrating the wide angle function of the optical system into the input lens group. As discussed above, optical system 28 does not form an intermediate poor quality image within or after input lens group 2810 and forms a high-resolution image on the image plane 2834. Such arrangement facilitates faster full surface imaging within short object-image working distances and with low distortion and aberrations, particularly at the edges of the image field.

According to an embodiment, there is provided an optical system comprising: a wide angle input lens group configured to receive radiation from an object surface and produce imageable radiation therefrom, such that there is no intermediate focused image formed within or after the wide angle input lens group; and an output lens group configured to receive the imageable radiation from the wide angle input lens group and focus the imageable radiation onto an image plane to image at least part of the object surface.

In an embodiment, the wide angle input lens group is configured to receive radiation having an angular spread of at least about 60 degrees. In an embodiment, the object is selected from the group consisting of: a reticle, a pellicle associated with a reticle, a substrate, and a holder, chuck or table in a lithography system. In an embodiment, the image plane is coplanar with a detector configured to receive the image of the at least part of the object surface and, based on the received image, detect contamination, an abnormality of the object surface, and/or a pattern on the object surface. In an embodiment, the wide angle input lens group comprises a front optical element and a wide angle input lens group doublet having an aspheric surface. In an embodiment, the aspheric surface is on the output side of the wide angle input lens group doublet. In an embodiment, the output lens group comprises a doublet and a last lens element having an aspheric surface. In an embodiment, the aspheric surface is on the input side of the last lens element. In an embodiment, the optical system is arranged to be not telecentric. In an embodiment, the wide angle input lens group and output lens group are configured to be interchangeably arranged in the optical system to change the magnification of the optical system.

In an embodiment, there is provided an inspection system to inspect a surface of an object, the inspection system comprising: an optical system comprising: a wide angle input lens group configured to receive radiation from the object surface and produce imageable radiation therefrom, such that there is no intermediate focused image formed within or after the wide angle input lens group; and an output lens group configured to receive the imageable radiation from the wide angle input lens group and focus the imageable radiation onto an image plane to image at least part of the object surface; and a detector configured to receive the image of the at least part of the object surface and, based on the received image, detect contamination, an abnormality of the object surface, and/or a pattern on the object surface.

In an embodiment, the optical system is configured to receive radiation having an angular spread of at least about 60 degrees. In an embodiment, the object is selected from the group consisting of: a reticle, a pellicle associated with a reticle, a substrate, and a holder, chuck, or table in a lithography system. In an embodiment, the pattern includes a bar code on a reticle.

In an embodiment, there is provided a lithographic apparatus comprising: a support structure configured to hold a patterning device, the patterning device configured to impart the beam with a pattern in its cross-section; a substrate table configured to hold a substrate; a projection system to project the patterned beam onto a target portion of the substrate; and an inspection system to inspect an object surface, the inspection system comprising: an optical system comprising: a wide angle input lens group configured to receive radiation from the object surface and produce imageable radiation therefrom, such that there is no intermediate focused image formed within or after the wide angle input lens group; and an output lens group configured to receive the imageable radiation from the wide angle input lens group and focus the imageable radiation onto an image plane to image at least part of the object surface; and a detector configured to receive the image of the at least part of the object surface and, based on the received image, detect contamination, an abnormality of the object surface, and/or a pattern on the object surface.

In an embodiment, the object is selected from the group consisting of: a patterning device, a pellicle associated with a patterning device, a substrate or a holder, chuck or table in a lithography system. In an embodiment, the angle-of-view of the wide angle lens group is at least about 60 degrees. In an embodiment, there is provided a manufacturing method, comprising:

projecting a patterned beam of radiation onto a target portion of a substrate; and inspecting an object surface, the inspecting comprising: receiving radiation from the object surface at a wide angle input lens group to produce imageable radiation therefrom, such that there is no intermediate focused image formed within or after the wide angle input lens group; focusing the imageable radiation from the wide angle input lens group onto an image plane to image at least part of the object surface; and detecting contamination, an abnormality of the object surface, and/or a pattern on the object surface based on the image of the at least part of the object surface.

In an embodiment, the object is selected from the group consisting of: a patterning device, a pellicle associated with a patterning device, a substrate or a holder, chuck or table in a lithography system. In an embodiment, the angle-of-view of the wide angle lens group is at least about 60 degrees.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers, Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The lithographic apparatus may also be of a type wherein a surface of the substrate is immersed in a liquid having a relatively high refractive index, e.g. water, so as to fill a space between a final element of the projection system and the substrate. Immersion liquids may also be applied to other spaces in the lithographic apparatus, for example, between the patterning device and a first element of the projection system. Immersion techniques are well known in the art for increasing the numerical aperture of projection systems.

The terms "radiation" and "beam" used herein encompass all types of electromagnetic radiation, including ultraviolet (UV) radiation (e.g. having a wavelength of or about 365, 248, 193, 157 or 126 nm) and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions configured to cause performance of a method as disclosed above, or a computer-readable data storage medium (e.g. semiconductor memory, magnetic or optical disk) having such a computer program stored therein.

The descriptions above are intended to be illustrative, not limiting. Thus, it will be apparent to those skilled in the art that modifications may be made to the invention as described without departing from the scope of the claims set out below.

What is claimed is:

1. A system comprising:
   an optical relay system comprising:
      an input condenser including a wide angle lens as a first lens element which is configured to receive radiation from a surface of an object, the input condenser configured to produce imageable radiation therefrom, such that there is no intermediate focused image formed within or after the input condenser, and
      an output lens group configured to receive the imageable radiation from the input condenser and focus the imageable radiation onto an image plane to image at least part of the object surface; and
   a detector configured to receive the image of the at least part of the object surface and, based on the received image, detect contamination, an abnormality of the object surface, and/or a pattern on the object surface, wherein the image plane is coplanar with a detector surface.

2. The system of claim 1, wherein the object is selected from the group consisting of: a reticle, a pellicle associated with a reticle, a substrate, and a holder, chuck or table in a lithography system.

3. The system of claim 1, wherein the input condenser comprises an input doublet having an aspheric surface.

4. The system of claim 3, wherein the aspheric surface is on the output side of the input doublet.

5. The system of claim 3, wherein the output lens group comprises an output doublet and a lens element having an aspheric surface.

6. The system of claim 5, wherein the aspheric surface is on the input side of the lens element.

7. The system of claim 1, wherein the input condenser is configured to receive radiation having an angular spread of at least about 60 degrees.

8. The system of claim 1, wherein the input condenser has a finite working distance to the object of about 270 mm or less.

9. The system of claim 1, wherein the optical relay system is arranged to be not telecentric.

10. The system of claim 1, wherein the input condenser and output lens group are configured to be interchangeably arranged in the optical relay system to change the magnification of the optical relay system.

11. The system of claim 1, wherein the output lens group comprises an output condenser.

12. A system comprising:
   an optical relay system comprising:
      an input condenser including a wide angle lens as a first lens element which is configured to receive radiation from a surface of an object, the input condenser configured to produce imageable radiation therefrom, such that there is no intermediate focused image formed within or after the input condenser, and
      an output lens group configured to receive the imageable radiation from the input condenser and focus the imageable radiation onto an image plane to image at least part of the object surface; and
   a detector configured to receive the image of the at least part of the object surface and, based on the received image, detect contamination, an abnormality of the object surface, and/or a pattern on the object surface, wherein the object is selected from the group consisting of: a reticle, a pellicle associated with a reticle, a substrate, and a holder, chuck or table in a lithography system.

13. The system of claim 12, wherein the system comprises a lithographic apparatus comprising a substrate table configured to hold a substrate and a projection system to project a patterned beam onto a target portion of the substrate.

14. The system of claim 12, wherein the input condenser is configured to receive radiation having an angular spread of at least about 60 degrees.

15. The system of claim 12, wherein the input condenser comprises an input doublet having an aspheric surface.

16. The system of claim 12, wherein the output lens group comprises an output doublet and a lens element having an aspheric surface.

17. The system of claim 12, wherein the input condenser has a finite working distance to the object of about 270 mm or less.

18. A manufacturing method, comprising:
projecting a patterned beam of radiation onto a target portion of a substrate; and
inspecting an object surface, the inspecting comprising:
- receiving radiation from the object surface at an input condenser of an optical system, the input condenser including a wide angle lens as a first lens element to produce imageable radiation therefrom, such that there is no intermediate focused image formed within or after the input condenser in the optical system;
- focusing the imageable radiation from the input condenser using an output lens group onto an image plane to image at least part of the object surface; and
- detecting contamination, an abnormality of the object surface, and/or a pattern on the object surface using a detector based on the image of the at least part of the object surface, wherein the object is selected from the group consisting of: a patterning device, a pellicle associated with a patterning device, a substrate, and a holder, chuck or table in a lithography system.

19. The method of claim 18, wherein the input condenser receives radiation having an angular spread of at least about 60 degrees.

20. The method of claim 18, comprising using the input condenser within a finite working distance to the object of about 270 mm or less.

* * * * *